United States Patent [19]

Eugster et al.

[11] Patent Number: 5,629,302
[45] Date of Patent: May 13, 1997

[54] BIOTENSIDE ESTERS AND PHOSPHATIDES WITH VITAMIN-D AND VITAMIN-E COMPOUNDS; PROCESSES FOR THEIR PREPARATION; SPONTANEOUSLY DISPERSIBLE AGENTS CONTAINING THESE COMPOUNDS, AND THEIR USE FOR THE TREATMENT OF TUMORS

[75] Inventors: Carl Eugster, Riehen; Conrad Hans Eugster, Wallisellen; Walter Haldemann, Binningen, all of Switzerland; Giorgio Rivara, Turin, Italy

[73] Assignee: Marigen S.A., Riehen, Switzerland

[21] Appl. No.: 479,633

[22] Filed: Jun. 7, 1995

Related U.S. Application Data

[62] Division of Ser. No. 312,980, Sep. 30, 1994, Pat. No. 5,502,224, which is a continuation of Ser. No. 42,251, Apr. 2, 1993, abandoned.

[30] Foreign Application Priority Data

Jun. 4, 1991 [CH] Switzerland .................. 01662191

[51] Int. Cl.$^6$ .................. C07C 401/00; A61K 31/59
[52] U.S. Cl. .................. 514/167; 552/653
[58] Field of Search .................. 552/653; 514/167

[56] References Cited

U.S. PATENT DOCUMENTS

| 4,206,131 | 6/1980 | Salmond | 552/653 |
| 4,263,215 | 4/1981 | Hasse et al. | 552/653 |

FOREIGN PATENT DOCUMENTS

| 0008573 | 3/1980 | European Pat. Off. |  |
| 0231777 | 8/1987 | European Pat. Off. |  |
| 2532000 | 2/1976 | Germany |  |
| 536602 | 5/1941 | United Kingdom |  |
| 9105754 | 5/1991 | WIPO |  |
| 9221670 | 12/1992 | WIPO | C07D 311/72 |

OTHER PUBLICATIONS

Nakamura et al., "Studies on tocopheral derivatives: V. Intestional absorption of several d, 1-3, 4-3H2-alpha-tocophenyl esters in the rat", Lipids, Band 10, Nr. 10, Oct. 1975, pp. 627-633.

Demole, et al., "Uber Ester des alpha-Tocopherols", Helvetica Chimica Acta, Band 22, Nr. 1, 1939, pp. 65-67, columns 3-4.

V. E. Ashirova et al., Chemical Abstracts, 108(15): 132119d (Apr. 11, 1988).

Chemical Abstracts, 85(17): 124243r (Oct. 1976).

D. R. Fraser et al., Chemical Abstracts, 68(17): 76143y (Apr. 22, 1968).

D. R. Fraser et al., Chemical Abstracts, 68(17): 76144z (Apr. 22, 1968).

W. Mueller–Mulot, et al., Chemical Abstracts, 93(24): 225681t (Dec. 15, 1980).

S. Stamatov et al., Chemical Abstracts, 113(19): 172422g (Nov. 5, 1990).

Fraser et al., Biochem. J. 106(2), 485–490 (1968).

Fraser et al., IBID, 106(2), 491–496 (1968).

*Primary Examiner*—Kimberly J. Prior
*Attorney, Agent, or Firm*—Foley & Lardner

[57] ABSTRACT

New biotenside esters and phosphatides formed with Vitamin-D and Vitamin-E compounds possessing a pronounced antitumor activity, processes for their production as well as for the preparation of concentrates and pharmaceutical compositions containing these new esters and phosphatides, and their use for treating tumors are described.

11 Claims, No Drawings

BIOTENSIDE ESTERS AND PHOSPHATIDES WITH VITAMIN-D AND VITAMIN-E COMPOUNDS; PROCESSES FOR THEIR PREPARATION; SPONTANEOUSLY DISPERSIBLE AGENTS CONTAINING THESE COMPOUNDS, AND THEIR USE FOR THE TREATMENT OF TUMORS

This application is a divisional of application Ser. No. 08/312,980, filed Sep. 30, 1992, now U.S. Pat. No. 5,502,224, which is a continuation of 08/042,251 filed Apr. 2, 1993, now abandoned.

INTRODUCTION

The present invention concerns new Esters and Phosphatides with Vitamin-D and Vitamin-E compounds, processes for their production as well as for the preparation of spontaneously dispersible concentrates and pharmaceutical compositions containing these compounds, and their use for the treatment of tumours.

Surprisingly it has been found that the newly synthetized Esters and Phosphatides with Vitamin-D and Vitamin-E compounds possess outstanding antitumour properties, particularly if these compounds are being incorporated into spontaneously dispersible concentrates.

DESCRIPTION OF THE INVENTION

The new Esters and Phosphatides with Vitamin-D and Vitamin-E compounds correspond to the general formulae (I) to (VI):

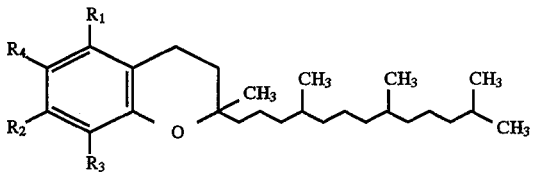
(I)

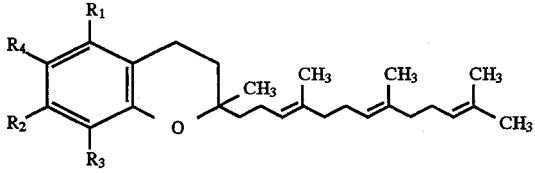
(II)

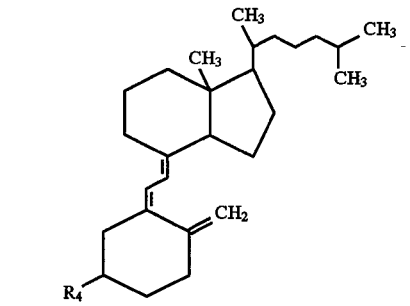
(III)

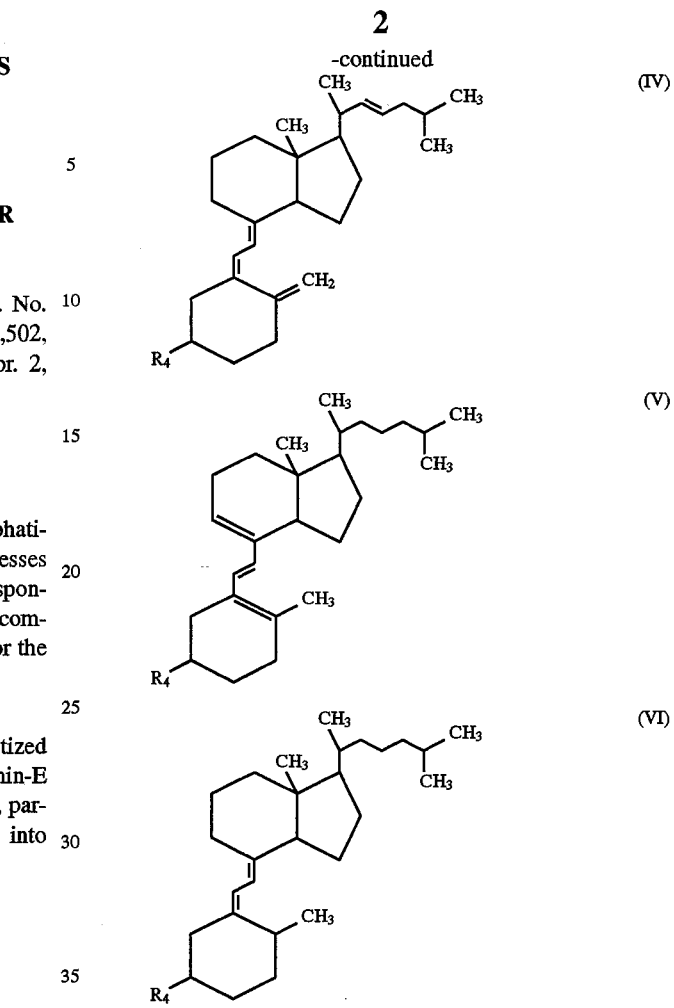

whereby in the formulae (I) and (II) the radicals $R_1$, $R_2$ and $R_3$ stand for hydrogen or methyl and the radical $R_4$ of the formulae (I) to (VI) determines a $C_1$ to $C_{32}$-alkylcarboxyl, and a $C_2$- to $C_{32}$-alkenylcarboxyl or alkapolyencarboxyl group respectively or a group of the formulae (VII) and (VIII) respectively:

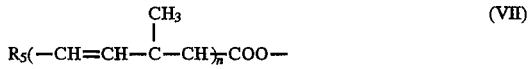
(VII)

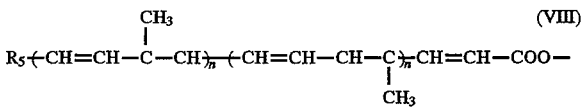
(VIII)

in which n designates the number 1, 2, 3, 4 or 5 and $R_5$ stands for a radical of the following formulae:

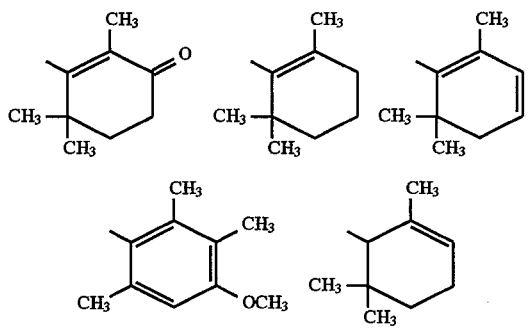

-continued

[chemical structures shown]

or represents the group of the formula (IX):

$$\begin{array}{l} CH_2-COOR_6 \\ | \\ CH-COOR_6 \\ | \quad\quad\quad O \\ | \quad\quad\quad || \\ CH_2-O-P-O- \\ \quad\quad\quad\quad | \\ \quad\quad\quad\quad X[-]\,Na[+] \end{array}$$ (IX)

in which $R_6$ denotes a $C_1$- to $C_{32}$-alkyl or a $C_2$- to $C_{32}$-alkenyl group and X represents an oxygen, sulfur or selenium atom, with the proviso that α-tocopherylesters formed with saturated or unsaturated carbonic acids having 14 to 22 carbon atoms are excluded.

The group of the formulae (VII) and (VIII) may have different stereoisomeric or rotational forms.

The class of the Vitamin-D compounds comprises the following chemical compounds:

Cholecalciferol: (5Z, 7E)-(3S)-9,10-seco-5,7,10 (19)-cholestatrien-3-ol 25-hydroxycholecalciferol [Calcidiol]:
(5Z, 7E)-(3S)-9,10-seco-5,7,10 (19)-cholestatrien-3,25-diol 1a-dehydroxy-cholecalciferol [Calcitriol]:
(5Z, 7E)-(1S, 3R)-9,10-seco-5,7,10 (19)-cholestatrien-1,3,25-triol Ergocalciferol [Calciol]:
(5Z, 7E, 22E)-(3S)-9,10-seco-5,7,10 (19),22-ergostatetraen-3-ol Tachysterol: (6E)-(3S)-9,10-seco-5, (10)-6,8-cholestatrien-3-ol Dehydrotachysterol: (5E, 7E)-(3S, 10S)-9,10-seco-5,7-cholestatrien-3-ol The class of the Vitamin-E compounds comprises all tocol- and tocotrienol-compounds, such as, e.g.:

Tocol [2-methyl-2(4,8,12-trimethyltridecyl)chroman-6-ol]

α-Tocopherol [5,7,8-trimethyltocol], which can take on the following configurations:
12,12,12-α-tocopherol
2-epi-α-tocopherol
2-ambo-α-tocopherol
all-rac-α-tocopherol
4-ambo-8-ambo-α-tocopherol β-Tocopherol [5,8-dimethyltocol]

γ-Tocopherol [7,8-dimethyltocol]

δ-Tocopherol [8-methyltocol]

Tocotrienol [2-methyl-2-(4,8,12-trimethyldeca-3,7,11-trianyl)chroman-6-ol]

ρ1-oder ρ2-Tocopherol [5,7,8-trimethyltocotrienol] and

ε-Tocopherol [5,8-dimethyltocotrienol or ε-tocotrienol]

The alkylcarboxyl, alkenycarboxyl or alkapolyencarboxyl groups at $R_4$, as well as the alkyl, alkenyl or alkapolyen groups at $R_6$ can be straight chained or branched. Alkapolyen means the corresponding alkadiene, alkatriene, alkatetraene, alkapentaene, alkahexaene and alkaheptaene compounds respectively.

Examples of such groups are, e.g.:

$CH_3-CH=CH-$
$CH_3-(CH_2)_3-CH_2-$
$CH_3-(CH_2)_{13}-CH_2-$
$CH_3-(CH_2CH=CH)_3-(CH_2)_6-CH_2-$
$CH_3-(CH_2)_3-(CH_2-CH=CH)_3-(CH_2)_6-CH_2-$
$CH_2=CH-(CH_2)_7-CH_2-$

[branched chain structures]

Important groups according to formula (VII) are characterized by the formulae (X), (XI) and (XII) respectively:

[structures X, XI, XII]

The group of the formula (X) may have different stereoisomeric forms, such as e.g. the all trans, the 9-cis or the 13-cis form.

Examples of the inventive new esters and phosphatides with vitamin-D and vitamin-E compounds are, inter alia:

Cholecalciferol-caproylate
Ergocalciferol-caproylate
Cholecalciferol-10-undecenoate
Ergocalciferol-10-undecenoate
Cholecalciferol-laurate Ergocalciferol-laurate
Cholecalciferol-palmitate
Ergocalciferol-palmitate
Cholecalciferol-linoleate
Ergocalciferol-linoleate
Cholecalciferol-linolenate
Ergocalciferol-linolenate
Cholecalciferol-all trans-retinate
Ergocalciferol-all trans-retinate
Cholecalciferol-3-ol-1,2,-dipalmitoylglycero-phosphatide
Cholecalciferol-3-ol-1,2,-dipalmitoylglycero-thiophosphatide
Cholecalciferol-geranyl-phosphatide
Cholecalciferol-farnesyl-phosphatide
Ergocalciferol-3-ol-1,2,-dipalmitoyl-glycero-phosphatide
Ergocalciferol-3-ol-1,2,-dipalmitoyl-glycero-thiophosphatide
Ergocalciferol-geranyl-phosphatide
Ergocalciferol-farnesyl-phosphatide
DL-α-Tocopherol-10-undecenoate
DL-α-Tocopherol-palmitate
DL-α-Tocopherol-all trans-retinate
DL-α-Tocopherol-13 cis-retinate

PREPARATION

The new sterolesters and sterolphosphatides with vitamin-D and vitamin-E compounds of the formulae (I) to (VI) may generally be prepared in semi-synthetic procedure by the following processes, which are known per se:

a) Reaction of a compound of the formula (XIV) or (XV):

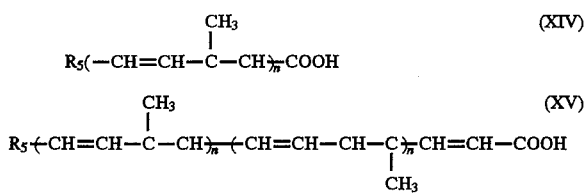

wherein n represents the numbers 1, 2, 3, 4 or 5 and $R_5$ stands for one of the following radicals:

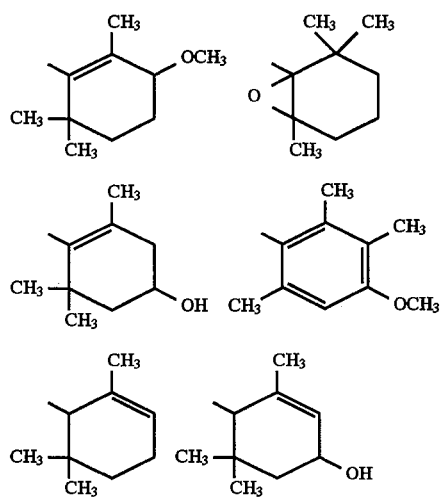

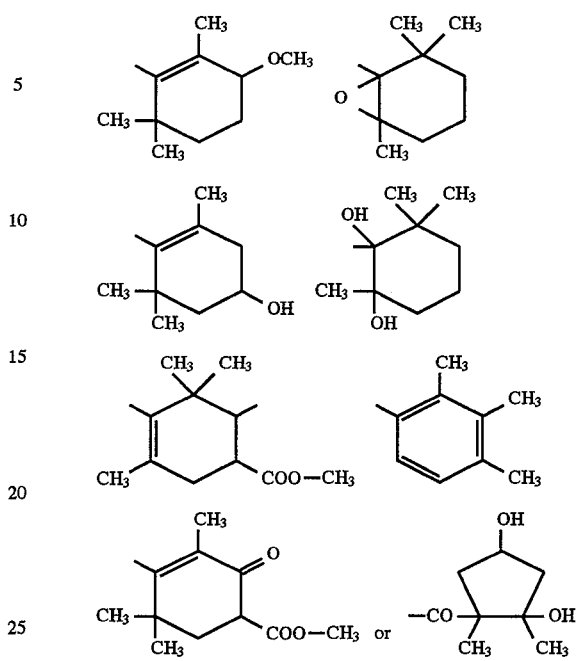

with N,N'-carbonyl-diimidazole at 25° to 70° C. with the addition of a catalytic amount of an alcoholate in tetrahydrofurane, benzene, chloroform or dimethylformamide or in a similar indifferent solvent, followed by alcoholysis of the imidazolides formed with a vitamin-D or vitamin-E compound.

b) Formation of the chloride or the bromide of a compound of the formulae (XIV), (XV) or (XVI):

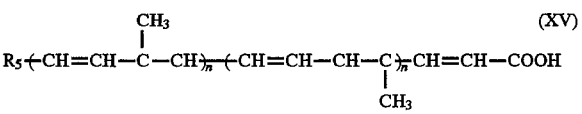

in which $R_6$ means a $C_1$- to $C_{32}$-alkyl or a $C_2$- to $C_{32}$-alkenyl and a $C_2$- to $C_{32}$-alkapolyene group respectively, with a chlorination or bromination agent such as thionylchloride, oxalylchloride or oxalylbromide, followed by the reaction of the chloride or bromide formed with a vitamin-D or a vitamin-E compound at a temperature of between 40° and 120° C. in an indifferent solvent such as toluene or xylene, and in the presence of a catalyst such as dimethylformamide or p-dimethylaminopyridine.

d) Esterification of a compound of the formula (XVII):

in which $R_6$ signifies a $C_1$- to $C_{32}$-alkyl group or a $C_2$- to $C_{32}$-alkenyl/alkapolyene group, in an inert solvent such as pyridine, tetrahydrofurane or chloroform, at a temperature of 20° C. with pivaloylchloride, followed by the reaction of the product in the same solvent with a vitamin-D or a vitamin-E compound.

The novel esters and phosphatides with vitamin-D and vitamin-E compounds possess, surprisingly, excellent anti-tumour activity, most notably when these compounds have been incorporated into spon-taneously dispersible concentrates. For this reason, spontaneously dis-persible concentrates made up with the new esters and phosphatides of vitamin-D and vitamin-E compounds of the formulae (I) to (VI) are also a subject matter of the present invention. When treated with water, such concentrates render microemulsions having excellent phase stability as well as much improved membrane permeability and spreading properties.

These spontaneously dispersible concentrates prepared in accordance with the invention contain 0.001 to 25% by weight of individual esters or phosphatides of vitamin-D or vitamin-E compounds or combinations of these compounds 0.001 to 40% by weight of a solvent or solvent mixture which is pharmaceutically acceptable and acts as a hydrotropic or coemulsifier 0.001 to 90% by weight of a pharmaceutically acceptable surfactant or surfactant mixture, and optionally up to 10% by weight of a vitamin or provitamin up to 10% by weight of a free fatty acid, and if appropriate, customary excipients and/or diluents.

The surfactants or surfactant mixtures to be employed according to the invention can be anionic, cationic, amphoteric or non-ionic. Ideally, they are non-ionic and have an HLB-value (i.e. a hydrophilic-lipophilic balance) of between 2 and 18; preferably, it is between 2 and 6 on the one hand and 10 and 15 on the other hand. HLB values describe the hydrophilic and lipophilic properties of an emulsifier. In this context see "Hydrophile-Lipophile Balance: History and recent Developments" by Paul Becher in Journal of Dispersion Science and Technology, 5 (1), 81–96 (1984).

Suitable anionic surfactants can be both so-called water-soluble soaps and water-soluble synthetic compounds.

Suitable soaps are the alkali metal salts, alkaline earth metal salts or optionally substituted ammonium salts of higher fatty acids ($C_{12}$ to $C_{22}$), for example the natural Na or K salts of oleic or stearic acids, or of natural mixtures of fatty acids which can be obtained, inter alia, from coconut oil or tallow oil. Other surfactants which may be mentioned are fatty acid methyltaurine salts, and modified and non-modified phospholipids.

However, more frequently used surfactants are so-called synthetic surfactants, in particular fatty sulfonates, fatty sulfates, sulfonated benzimidazole derivatives or alkylaryl-sulfonates.

The fatty sulfonates and fatty sulfates are usually present in the form of alkali metal salts, alkaline earth metal salts or optionally substituted ammonium salts and generally have an alkyl radical containing 8 to 22 C atoms, alkyl also encompassing the alkyl moiety of acyl radicals. Examples are the Na or Ca salt of ligninsulfonic acid, of dodecylsulfuric ester and sulfonic acids of fatty alcohol/ethylene oxide adducts. The sulfonated benzimidazole derivatives preferably contain two sulfonyl groups and one fatty acid radical containing about 8 to 22 C atoms. Alkylarylsulfonates are, for example, the Na, Ca or triethanolamine salts of dodecylbenzenesulfonic acid, of dibutylnaphthalenesulfonic acid or of a naphthalenesulfonic acid/formaldehyde condensation product.

The non-ionic surfactants are mainly chosen from amongst the polyglycol ether derivatives of aliphatic or cycloaliphatic alcohols, saturated or unsaturated fatty acids and alkylphenols which can contain 3 to 30 glycol ether groups and 8 to 20 C atoms in the (aliphatic) hydrocarbon radical and 6 to 18 C atoms in the alkyl radical. Other suitable non-ionic surfactants are the water-soluble polyethyleneoxy-adducts onto polypropylene glycol and alkyl polypropylene glycol with 1 to 10 C atoms in the alkyl chain, which adducts contain 20 to 250 ethylene glycol ether groups and 10 to 100 propylene ether groups. The compounds which have been mentioned customarily contain 1 to 5 ethylene units per propylene glycol unit.

The following may be mentioned as examples of non-ionic surfactants: nonylphenol polyethoxyethanols, castor oil polyglycol ethers, polypropylene/polyethylene oxide adducts, tributylphenoxy-polyethoxy-ethanol, polyethyleneglycol and octylphenoxy-polyethoxyethanol. Moreover, fatty acid esters of polyoxyethylene-sorbitan, such as polyoxyethylene sorbitan trioleate, are also suitable.

The cationic surfactants are mainly quaternary ammonium salts which contain at least one alkyl radical having 8 to 22 C atoms as the N-substituent and which have lower, optionally halogenated alkyl radicals, benzyl radicals or lower hydroxyalkyl radicals as further substituents. The salts are mainly present in the form of halides, methylsulfates or ethylsulfates, for example stearyltrimethylammonium chloride or benzyldi-(2-chloroethyl)-ethylammonium bromide.

When preparing the inventive spontaneously dispersible concentrates, special preference is given to phosphoric acid ester tensides, such as:

Tristyrylphenolpolyoxyethylene-18-mono/dimethyl-phosphoric-acid-ester (Soprophor® FL, Rhône-Poulenc);
Nonylphenol-10-polyoxyethylene-mono/dimethylphosphoric-acid-ester (Diphasol® 3873, CIBA-GEIGY);

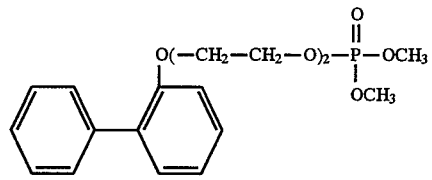

(Tensid 508, CIBA-GEIGY);
Tinovetin® JU (CIBA-GEIGY), a hydroxybiphenyl-10-ethoxy-phosphoric acid ester
Butyl-mono-4-ethoxy-phosphoric acid ester (Zerostat® AT, CIBA-GEIGY), and

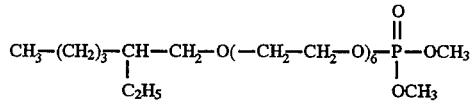

(Zerostat® AN, CIBA-GEIGY), respectively.

The following compounds may be employed as the pharmaceutically acceptable solvent which acts as the hydrotropic, or coemulsifier, for example: esters of an aliphatic alcohol ($C_3$ to $C_{18}$) with an aliphatic carboxylic acid ($C_{10}$ to $C_{22}$), such as isopropyl laurate, hexyl laurate, decyl laurate, isopropyl myristate and lauryl myristate; hydrocarbons having a straight carbon chain ($C_{12}$ to $C_{32}$) which is substituted by 6 to 16 methyl groups and which can have up to 6 double bonds, examples which may be mentioned being terpenes, such as polymethylbutanes and polymethylbutenes.

Monoesters of ethylene glycol or propylene glycol with an aliphatic carboxylic acid ($C_6$ to $C_{22}$), such as propylene glycol monolaurate and propylene glycol monomyristate.

Esters of an aliphatic alcohol ($C_{12}$ to $C_{22}$) with lactic acid, such as, for example, myristyl lactate or, preferably, lauryl lactate. Monoesters or diesters of glycerol with an aliphatic carboxylic acid ($C_6$ to $C_{22}$), such as, for example, glyceryl caprylate or Miglyol® 812 neutral oil (Oleum neutrale).

Esters of a poly(2-7)ethylene glycol glycerolether having at least one free hydroxyl group with an aliphatic carboxylic acid ($C_6$ to $C_{22}$), such as, for example, aliphatic alcohols ($C_{12}$ to $C_{22}$), thus, inter alia, dodecanol, tetradodecanol, oleyl alcohol, 2-hexyldecanol and 2-octyldecanol.

Esters containing at least one free hydroxyl group, of poly-(2-10)glycol with an aliphatic carboxylic acid ($C_6$ to $C_{22}$), monoethers of a polyethylene glycol with an aliphatic alcohol ($C_{12}$ to $C_{18}$), such as, for example, polyoxyethylene-($C_{10}$) octylether.

Heterocyclic compounds such as 1-methyl-2-pyrrolidon.

Before their application in the spontaneously dispersible concentrates all technical tensides have been cleaned by filtration or by chromatography over aluminum-oxide with an inert solvent as eluent, such as tetrahydrofurane, ethylalcohol or dichlormethane.

Suitable additives for the spontaneously dispersible concentrates according to the invention are vitamins and provitamins [such as, for example, vitamin A (retinoic acid), retinol, carotenes, tocopherols], and also free fatty acids, such as: valeric acid, isovaleric acid, sorbic acid, isocaproic acid, pelargonic acid, lauric acid, myristic acid, palmitic acid, stearic acid, arachidic acid, behenic acid, hexacosanoic acid, octacosanoic acid, pentadecanoic acid, decenylic acid, undecylenic acid, dodecenylic acid, oleic acid, linoleic acid, linolenic acid, arachidonic acid, erucic acid, etc.

The daily dose required for pharmaceutical administration is 0.001 to 25 mg/kg of body weight, if possible split into 2-3 individual doses. For this purpose, the new vitaminsterol esters sterol phosphatides, or the spontaneously dispersible concentrates with these compounds, can be incorporated into the conventional pharmaceutical preparations and dosage forms, such as coated tablets, tablets, capsules, powders, granules, pellets, solutions, ampuls, emulsions, creams or suppositories together with the customary excipients and/or diluents and stabilizers.

The active substances or mixtures of active substances which form the subject-matter of the invention, and the spontaneously dispersible concentrates which contain these active substances or mixtures of active substances, can be administered to humans orally, by injection (intravenously, subcutaneously or intramuscularly) or in other ways. If they are presented as solid dosage forms for oral administration, this can be in the form of tablets, granules, pellets, powders or capsules, etc. The preparations can contain additives, for example a pharmaceutical excipient, such as a saccharide or cellulose base, a binder, such as starch paste or methylcellulose, a filler, or a disintegrant, etc., with additives being employed which are customarily used in the preparation of medicinal or pharmaceutical formulations. When the active substances or mixtures of active substances according to the invention are administered orally in the form of liquid dosage forms, they can be present in any form selected from amongst aqueous preparations for internal use, from suspensions, emulsions and syrups, etc., and they can also be present in the form of dried preparations which are dissolved or emulsified prior to use.

When the active substances or mixtures of active substances according to the invention are processed in the form of aqueous solutions, suspensions or oily or aqueous emulsions, preferably microemulsions, from the spontaneously dispersible concentrates according to the invention, they can also be injected. However, it is customary to prepare the injection solutions shortly before administration, by dissolving or suspending the extracts or concentrates in aqueous, liquid media, such as sterile water or physiological sodium chloride solution or glucose solution.

If required, conventionally used solvents, stabilizers, preservatives and additives for the preparation of isotonic solutions can be added to a preparation for injection. The preparations for injection obtained in this manner are administered intravenously, intramuscularly, subcutaneously or in any other suitable way.

The present invention also relates to pharmaceutical preparations which contain the active substances, or mixtures of active substances, or the spontaneously dispersible concentrates, which have been above described, for controlling the growth of tumour cells. The pharmaceutical preparations according to the invention are those which can be used for enteral (such as oral or rectal) or for parenteral or topical administration to warm-blooded animals, which preparations contain the spontaneously dispersible concentrate on its own or together with a pharmaceutically acceptable excipient.

The dosage of the concentrates according to the invention depends on the warm-blooded species, on the age and on the individual condition, and on the mode of administration. For example, doses in the range of about 0.1-50 mg/kg of body weight are administered subcutaneously, and doses in the range of 0.05-5 mg/kg of body weight are administered intraperitoneally to warm-blooded animals having a low body weight, such as, for example, mice, rats and hamsters, to achieve an effect of tumour cell destruction.

The oral and rectal forms of the novel pharmaceutical preparations contain between 1 and 95%, preferably between 10 end 95%, and in particular between 20 and 95%, of the spontaneously dispersible concentrate according to the invention. For example, they can be present in unit-type dosage forms, i.e., as coated tablets, micropellets, tablets, suppositories or ampuls and, in particular, as capsules.

Suitable pharmaceutically acceptable excipients for the oral forms are mainly fillers, such as sugars (for example lactose, sucrose, mannitol or sorbitol), cellulose preparations and/or calcium phosphates (for example tricalcium phosphate or calcium hydrogen phosphate), furthermore binders, such as starch paste, with the use of, inter alia, corn starch, wheat starch, rice starch or potato starch, gelatine, tragacanth, methylcellulose, hydroxymethylcellulose, sodium carboxymethylcellulose and/or polyvinylpyrrolidone and/or disintegrants (if desired), such as the above mentioned starches, furthermore carboxymethyl starch, crosslinked polyvinylpyrrolidone, agar, alginic acid or a salt thereof, for example sodium alginate.

Examples of suitable flow-control agents are the polyethylene glycols Nos. 200–600 and above.

The gelatine capsules, which are still the preferred dosage form for humans, are provided with suitable coatings, concentrated sugar solutions [which can optionally contain gum arabic, talc, polyvinylpyrrolidone, polyethylene glycol and/or titanium dioxide], lacquer solutions (aqueous or those which have been prepared using organic solvents), or enteric coatings of solutions of suitable cellulose preparations, such as microcrystalline cellulose (Avicela), acetylcellulose phthalate, hydroxymethylcellulose-phthalate, Metolose®, AQOAT® or a copolymer, such as Eudragit® L 30 D, being used, inter alia.

Pharmaceutical dosage forms for oral use which are particularly suitable according to the invention are two-piece gelatine capsules with a plasticizer, such as glycerol or sorbitol. The soft-gelatine or hard-gelatine capsules and the capsules made of AQOAT® hydroxypropyl methylcellulose respectively can contain the spontaneously dispersible concentrate according to the invention as a mixture with fillers, such as lactose, binders, such as starch, and/or glidants, such as talc or magnesium stearate, and, if appropriate, together with stabilizers and antioxidants, such as, for example, α-, β- or γ-tocopherol. It may be expedient to employ suitable liquids, such as liquid polyethylene glycols Nos. 200 to 600 as diluents, to which stabilizers and antioxidants can also be added.

The spontaneously dispersible concentrates may be incorporated into a therapeutic system containing 44 parts of core material for granules and pellets, 25 parts of the spontaneously dispersible concentrate and 31 parts of an enteric and slow-release coating made from hydroxylpropyl-methylcellulose-acetate-succinate. The therapeutic system preferably contains 64 parts of a core material for granules and pellets and 36 parts of the spontaneously dispersible concentrate.

For parenteral administration, distilled water is added to the concentrates according to the invention. To the aqueous microemulsion for injection which then forms, there can be added viscosity-increasing substances, for example Na-carboxymethyl-cellulose, sorbitol, mannitol and/or dextran, and if appropriate also stabilizers and antioxidants.

The pharmaceutical preparations for parenteral administration preferably contain between 0.1 and 60%, especially between 1 and 40%, of the spontaneously dispersible concentrate according to the invention.

Suitable preparations for topical use, which are particularly suitable for the prophylaxis and the treatment of cancers of the skin, are, for example, creams, ointments, pastes, foams, tinctures and solutions, which contain between 0.001 and 70% of the concentrate according to the invention.

Oily bases which are used for creams and oil-in-water emulsions which contain more than 50% water, are mainly fatty alcohols, for example lauryl alcohol, cetyl alcohol or stearyl alcohol, waxes of liquid to solid consistency, for example isopropyl myristate, wool wax or beeswax and/or hydrocarbons, such as, for example, petroleum jelly (petrolatum) or paraffin oil. Substances which are mainly suitable for emulsifying these oily bases are surface-active, pharmaceutically acceptable substances having predominantly hydrophilic properties, such as, for example, non-ionic emulsifiers, in particular fatty acid esters of polyalcohols or ethylene oxide adducts (such as polyglycerol fatty acid esters or polyethylene sorbitan fatty acid esters) having an HLB value of less than 8. Additives which are added to the water phase are, inter alia, agents which prevent desiccation of the creams, for example polyalcohols, such as glycerol, sorbitol, propylene glycol and/or polyethylene glycols Nos. 200 to 600, and furthermore preservatives, odor-imparting substances, etc.

Ointments are water-in-oil emulsions which contain up to 70%, but preferably between 20 and 50%, water or aqueous phases.

Substances which are suitable as the lipid phase are mainly hydro-carbons, for example petroleum jelly, paraffin oil and/or solid paraffins, which contain hydroxy compounds suitable for improving the water-binding capacity, for example fatty alcohols or esters, such as cetyl alcohol or wool wax alcohols.

In some cases, emulsifiers having an HLB-value of 8 to 16, such as, for example, sorbitan fatty acid esters (such as sorbitan isostearol) are also added. Additives which are added to the water phase are, inter alia, humectants, such as polyalcohols (glycerol, propylene glycol, sorbitol and/or polyethylene glycols No. 200, 400, 600); and furthermore preservatives, odor-imparting substances, etc.

Fatty ointments are anhydrous and chiefly contain hydrocarbons as the base, for example paraffin, petroleum jelly and/or liquid paraffins; moreover natural or partially-synthetic fats, such as, for example, coconut fatty acid triglyceride, furthermore: fatty acid partial esters of glycerol, such as, for example, the fatty alcohols, emulsifiers and/or additives which increase the water-absorption capacity, all of which have been mentioned in connection with the ointments.

Pastes are creams and ointments containing powder constituents which absorb secretions, such as, for example, metal oxides (such as titanium oxide or zinc oxide), and furthermore talc and/or aluminum silicates whose task it is to bind any moisture or discharge which may be present.

Foams are administered from pressurized containers and are oil-in-water emulsions of the spontaneously dispersible concentrates according to the invention which are present in aerosol form, with halogenated hydrocarbons (such as, for example, lower chloro-fluoroalkanes; such as dichlorodifluoromethane and dichlorotetrafluorethane) being added as propellants. Other substances which may be added are the customary additives, such as preservatives, etc.

The present invention also relates to the use of the active substances, mixtures of active substances and spontaneuosly emulsifiable concen-trates according to the invention for inhibiting the growth of tumour cells or as prophylactic agents against oncoses in humans and animals, administration preferably being carried out in the dosage forms which correspond to the pharmaceutical preparations described above. For use as dietary foods and as food additives, the optimum compositions must be established for every individual case.

Processing examples for inventive esters and phosphatides with vitamin-D and Vitamin-E compounds 1. Process for the Preparation of DL-α-Tocopherolpalmitate To a solution of 450 mg DL-α-Tocopherol and 50 mg dimethylformamide in 30 ml Toluene at 20° C. 350 mg palmitoylchloride (ca. 20% excess) are being added dropwise. The reaction mixture is heated to 80° C. and refluxed for 3 hours. Subsequently, the solvent is distilled off in vacuo and the residue is recrystallized in acetonitrile. DL-α-Tocopherolpalmitate is obtained in the form of crystals having a melting range of 53,8° to 55,2° C.

The following compounds are prepared in analogous manner:

| | |
|---|---|
| DL-α-Tocopherolpivaloylate | RI 1.50102 |
| DL-α-Tocopherolvalerate | RI 1.49528 |
| DL-α-Tocopherolcaprylate | UV 296,8 233,6 RI 1,48018 |
| DL-α-Tocopherolcrotonate | RI 1.50378 |
| DL-α-Tocopherol-10-undecenoate | UV 296,6 233,6 RI 1,49188 |
| DL-α-Tocopherol-2-dodecenoate | UV 296,4 233,0 RI 1,49388 |
| DL-α-Tocopherololeate | RI 1,48158 |
| Ergocalciferolpivaloylate | RI 1.52148 |
| Ergocalciferolvalerate | RI 1.53924 |
| Ergocalciferolcaprylate | UV 302,4 290,4 RI 1.53010 |
| Ergocalciferollaurate | UV 301.6 289,0 |
| Ergocalciferolpalmitate | RI 1.50316 |
| Ergocalciferolcrotonate | UV 300,4 288,6 RI 1.55342 |
| Ergocalciferol-10-undecenoate | UV 302,4 292,4 RI 1,50360 |
| Ergocalciferololeate | RI 1.52620 |
| Cholecalciferolpivaloylate | RI 1.51292 |
| Cholecalciferolvalerate | RI 1.52714 |

| | |
|---|---|
| Cholecalciferoicaprylate | RI 1,51756 |
| | IR 2931 cm$^{-1}$ ν(CH) |
| | 2870 cm$^{-1}$ ν(CH) |
| | 1772 cm$^{-1}$ ν(C=O) Ester |
| | 1467 cm$^{-1}$ δ(CH) |
| | 1370 cm$^{-1}$ δ(CH$_3$) |
| | 1171 cm$^{-1}$ ν(C—O) |
| | 959 cm$^{-1}$ δ(CH) Vinyliden |
| Cholecalciferolpalmitate | RI 1.51418 |
| | IR 2928 cm$^{-1}$ ν(CH) |
| | 2855 cm$^{-1}$ ν(CH) |
| | 1723 cm$^{-1}$ ν(C=O) Ester |
| | 1467 cm$^{-1}$ δ(CH) |
| | 1370 cm$^{-1}$ δ(CH$_3$) |
| | 1184 cm$^{-1}$ ν(C—O) |
| | 959 cm$^{-1}$ δ(CH) Olefinic OH |
| Cholecalciferolcrotonate | RI 1,55444 |
| | IR 2955 cm$^{-1}$ ν(CH) |
| | 1717 cm$^{-1}$ ν(C=O) Ester |
| | 1467 cm$^{-1}$ δ(CH) |
| | 1369 cm$^{-1}$ δ(CH$_3$) |
| | 1189 cm$^{-1}$ δ(C—O) |
| | 959 cm$^{-1}$ δ(CH) Olefinic CH |
| Cholecalciferol-10-undecenoate | RI 1,51796 |
| | IR 2931 cm$^{-1}$ ν(CH) |
| | 1725 cm$^{-1}$ ν(C=O) Ester |
| | 1458 cm$^{-1}$ δ(CH) |
| | 1371 cm$^{-1}$ δ(CH$_3$) |
| | 1179 cm$^{-1}$ ν(C—O) |
| | d(CH)} 974 cm$^{-1}$ {δ(CH) |
| | trans} 913 cm$^{-1}$ {δ(CH) of CH=CH$_2$ |
| Cholecalciferololeate | RI 1.52092 |
| | IR 2931 cm$^{-1}$ δ(CH) |
| | 1723 cm$^{-1}$ ν(C=O) Ester |
| | 1458 cm$^{-1}$ δ(CH) |
| | 1372 cm$^{-1}$ δ(CH3) |
| | 1187 cm$^{-1}$ ν(C—O) |
| | 973 cm$^{-1}$ δ(CH) trans |
| Cholecalciferol-all trans-retinate | NIR 1627 cm$^{-1}$ (C=C) [D$_3$] |
| | 1583 cm$^{-1}$ C=C |
| | [Retinate] |
| Cholecalciferolcrotonate | RI 1,55444 |
| Cholecalciferol-10-undecenoate | RI 1,55796 |
| Cholecalciferololeate | RI 1.52092 |

2. Preparation of Ergocalciferollinolenate

To a solution of 300 mg linolenic acid in 20 ml toluene at 10° C. 200 mg oxalylchloride in 30 ml toluene are being added dropwise. Subsequently, 10 ml toluene are being distilled off in vacuo and then 400 mg ergocalciferol and 50 mg dimethylformamide are added. Heat to 90° C. and reflux for 2 hours, then distill off the solvent on a Rotavapor. The residue is being chromatographed on a silicagel column with 80:20 cyclohexane/ethyl acetate.

Ergocalciferollinolenate is obtained, characterized by a Refractory Index (RI) n$_D$ 20° C. of 1,53986 and a UV-absorption maximum Imax at 291,8 nm.

IR 2931 cm$^{-1}$ δ(CH)

1723 cm$^{-1}$ ν(C=O) Ester 1458 cm$^{-1}$ δ(CH)

1372 cm$^{-1}$ δ(CH$_3$)

1187 cm$^{-1}$ ν(C—O)

973 cm$^{-1}$ δ(CH) trans

In analogous manner the following products can be prepared:

| | |
|---|---|
| DL-α-Tocopherololeate | RI 1,49302 |
| Cholecalciferollinolenate | RI 1,54030 |
| DL-α-Tocopherollinolenate | RI 1,48290 |
| Ergocalciferollinoleate | RI 1.53274 |
| Cholecalciferollinoleate | RI 1.52138 |

| | |
|---|---|
| DL-α-Tocopherollinoleate | RI 1.48888 |
| Ergocalciferol-all trans-retinate | UV 291,5 BI 1,49226 |
| | IR 2958 cm$^{-1}$ ν(CH) |
| | 2871 cm$^{-1}$ ν(CH) |
| | 1701 cm$^{-1}$ ν(C=O) Ester |
| | 1608 cm$^{-1}$ ν(C=C) |
| | 1583 cm$^{-1}$ ν(C=C) |
| | 1457 cm$^{-1}$ δ(CH) |
| | 1239 cm$^{-1}$ ν(C=O) |
| | 1153 cm$^{-1}$ ν(C=O) |
| | 1016 cm$^{-1}$ ν(C=O) |
| | 970 cm$^{-1}$ δ(CH) } |
| | trans C=C } |
| Cholocalciferol-all trans-retinat | Bf 1.48774 |
| | IR 2958 cm$^{-1}$ ν(CH) |
| | 2871 cm$^{-1}$ ν(CH) |
| | 1701 cm$^{-1}$ ν(C=O) Ester |
| | 1608 cm$^{-1}$ ν(C=C) |
| | 1583 cm$^{-1}$ ν(C=C) |
| | 1457 cm$^{-1}$ δ(CH) |
| | 1239 cm$^{-1}$ ν(C=O) |
| | 1153 cm$^{-1}$ ν(C=O) |
| | 1016 cm$^{-1}$ ν(C=O) |
| | 970 cm$^{-1}$ trans C=C |
| | δ(CH) |
| | NIR 1627 cm$^{-1}$ (C=C) [D$_3$] |
| | 1583 cm$^{-1}$ (C=C) [Ret.] |
| DL-α-Tocopherol-all trans-retinate | RI 1.55350 |
| | NIR 1583 cm$^{-1}$ (C=C) [Ret.] |
| Ergocalciferol-13 cis-retinate | NIR 1627 cm$^{-1}$ (C=C) [D$_2$] |
| | 1585 cm$^{-1}$ (C=C) [Ret.] |
| Cholecalciferol-13 cis-retinate | NIR 1627 cm$^{-1}$ (C=C) [D$_3$] |
| | 1583 cm$^{-1}$ (C=C) [Ret.] |
| DL-α-Tocopherol-13 cis-retinate | NIR 1583 cm$^{-1}$ (C=C) [Ret.] |

\*) N.B.:
RI = Refraction Index, measured on a DUR Refractometer Schmidt + Haensch, Berlin.
IR = Infrared Spectra measured on a Spectrophotometer Perkin-Elmer 683G
NIR = Near Infrared (FT RAMAN) Spectra measured on a spectrometer YAG Laser, Excitation at 1064 nm.
UV-Spectra measured on a Spectrophotometer Shimadzu UV-160A 3. Preparation of Ergocalciferol-azafrinate To a solution of 80 mg azafrinate, formula (XII) [process for preparing this compound vide Helv. Chim. Acta 58 (1975) 1722–1727 and Helv. Chim Acta 65 (1982) 353–354] in 50 ml chloroform 65 mg N,N'-carbonyl-diimidazol are added. The mixture is left standing for 12 hours at room temperature, then 40 mg ergocalciferol are added. After further standing for 12 hours at a temperature of 30° C. the solvent is distilled off and the residue diluted in 50 ml ethyl acetate. The solution is washed once with 1/10N hydrochloric acid and once with 1/10N sodium hydroxide and then the solvent is distilled off. The residue is chromatographed on a silicagel column; eluent: n hexane/ethyl acetate 9:1.

Ergocalciferol-azafrinate is obtained with a melting point of 171° to 173° C. and an UV absorption maximum of 429,5 nm.

4. Process for Preparing Ergocalciferol-1,2-dipalmitoyl-glycero-phosphatide and Ergocalciferol-1,2-dipalmitoyl-glycero-thiophosphatide 1,2-dipalmitoyl-glycero-3-H-phosphonate-triethylammonium salt is prepared according to the method of I. Lindth and J. Stawinski in J.Org.Chem 54, 1338–1342 (1989): "Synthesis of glycerophospholipids and their analogues via H-phosphonate".

The reaction product can be used for the next chemical step without any intermediary cleaning operation by chromatography.

600 mg of the reaction product and 600 mg ergocalciferol are dissolved in pyridine and brought to dryness in vacuo. The residue is again dissolved in 15 ml pyridine. After adding 0,2 ml pivaloylchloride, this solution is stirred 30 minutes in dry athmosphere. After further adding 0,1 ml pivaloyl-chloride the solution is again stirred for 30 minutes at room temperature.

The reaction solution is then divided into two parts: To the first part of this solution 150 mg jodine, dissolved in 2 ml pyridine-water 98:2, are added. After 30 minutes stirring at 20° C. the reaction mixture is poured in 50 ml chloroform. This solution is washed once with 20 ml 5% sodium-bisulfit-solution and twice with 20 ml water. After separation the chloro-form-phase is distilled off to dryness on a Rotavapor.

To the other part of the solution 150 mg sulfur in 2 ml pyridine-toluene 1:1 are added. The solution is stirred for 3 hours at a temperature of 20° C. 50 ml chloroform are added and then the solution is washed twice with 20 ml water. After the separation has taken place the chloroform-toluene-phase is distilled off to dryness on a Rotavapor.

The two raw products are chromatographed on a silicagel column with chloroform/hexane 2:1 and 8:1 as eluent.

The following products are obtained:
Ergocalciferol-1,2-dipalmitoyl-glycero-phosphatide, with a melting point of 168° to 170° C. and
Ergocalciferol-1,2-dipalmitoyl-glycero-thiophosphatide, with a (smectic) melting range of ca. 145° to 150° C.

In a corresping way the following compounds are also prepared:
Ergocalciferol-geranyl-phosphatide
Ergocalciferol-farnesyl-phosphatide
Cholecalciferol-geranyl-phosphatide
Cholecalciferol-farnesyl-phosphatide
DL-α-Tocopherol-geranyl-phosphatide
DL-α-Tocopherol-farnesyl-phosphatide Rf-values of inventive compounds which are being prepared according to the examples 1 to 4:

| | 1% solution in $CH_2Cl_2$, applied in bands 2 cm/2 μl Linomat III CAMAC 10 cm run UV 366 after 1:1 $H_2SO_4$/MeOH 2 min. 120° C. SYSTEM | | | | | | |
|---|---|---|---|---|---|---|---|
| COMPOUND | 1 | 2 | 3 | 4 | 5 | 6 | 7 |
| TOCO-C 8:0 | 0.04 | 0.02 | 0.09 | 0.28 | 0.59 | 0.36 | 0.18 |
| TOCO-C 11:1 | 0.04 | 0.25 | 0.09 | 0.28 | 0.59 | 0.36 | 0.18 |
| TOCO-C 16:0 | 0.14 | 0.08 | 0.33 | 0.78 | 0.96 | 0.83 | 0.59 |
| TOCO-trans-RET | 0.08 | 0.04 | 0.26 | 0.76 | 0.93 | 0.85 | 0.54 |
| TOCO-C 18:1 | 0.06 | 0.09 | 0.40 | 0.90 | 1.0 | 0.95 | 0.74 |
| $D_2$-C 16:0 | 0.25 | 0.13 | 0.35 | 0.89 | 1.0 | 1.0 | 0.88 |
| $D_2$-trans-RET. | 0.21 | 0.1 | 0.33 | 0.85 | 0.97 | 1.0 | 0.83 |
| $D_3$-C 11:1 | 0.22 | 0.13 | 0.42 | 0.87 | 0.88 | 0.92 | 0.75 |
| $D_3$-trans-RET | 0.15 | 0.14 | 0.41 | 0.89 | 1.0 | 0.94 | 0.79 |

EXPLANATION

System 1 Plate Merck Art. 5715 petrolether/diethylether 98:2
System 2 Plate Merck Art. 5715 petrolether/diethylether 97:3
System 3 Plate Merck Art. 5715 cyclohexane/ethylacetate 97:3
System 4 Plate Macherey Nagel RP 18 Art. 811'071 petrolether/diethylether 95:5
System 5 Plate Macherey Nagel RP 18 Art. 811'071 n hexane/t.butylmethylether/acetone 90:5:5
System 6 Plate Macherey Nagel RP 18 Art. 811'071 petrolether/cyclohexane/ethylacetate/$H_2O$ 48:48:3:1
System 7 Plate Macherey Nagel RP 18 Art. 811'071 petrolether/diethylether 97:3

Composition examples of spontaneously dispersible agents which contain as substances possessing antitumour activity vitamin sterolesters and/or vitamin-sterolphosphatide compounds according to the formulae (I) to (VI):

a) 0,5 to 25% by weight of one or several of the vitamin-sterolesters and/or vitamin-sterolphosphatide compounds of the formulae (I) to (VI)

0,1 to 40% by weight of isopropylmyristate, isopropylpalmitate or Miglyol® 812 (Dynamit Nobel)

20 to 45% by weight of emulsifier mixture Diphasol® 3873 (CIBA-GEIGY)

20 to 45% by weight of Invadin® JFC 800% (CIBA-GEIGY)

b) 0,5 to 25% by weight of one or several of the vitamin-sterolesters and/or vitamin-sterolphosphatide compounds of the formulae (I) to (VI)

0,1 to 40% by weight of isopropylmyristate, sopropylpalmitate or Miglyol® 812 (Dynamit Nobel)

20 to 45% by weight of Invadin® JFC 800% (CIBA-GEIGY)

20 to 45% by weight of Soprophor® FL (Rhône-Poulenc)

Miglyol® 812 is a neutral oil (oleum neutrale) of Dynamit Nobel, which is a triacylglycerol of the coconut fatty acids, the so-called fractionated, middle chained (C8 to C10) compounds [i.e. a caprylic/capric triglyceride in the CTFA classification].

Diphasol® 3873 (CIBA-GEIGY) (which is equivalent to SERMUL® EA188) is a surfactant mixture consisting of the following two compounds (50:50):

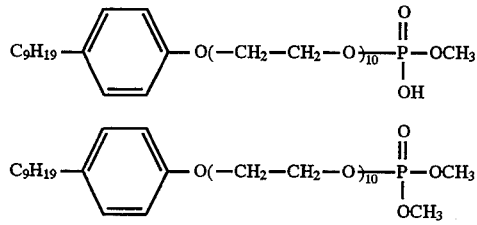

Invadin® JFC 800% (CIBA-GEIGY) is a tert. octylphenylpolyoxy-ethyleneether with 9 to 10 oxyethylene groups Soprophor® FL (Rhône-Poulenc) is a tristyrylphenolpolyoxy-ethylene-18-mono/dimethyl-phosphoracidester with formula:

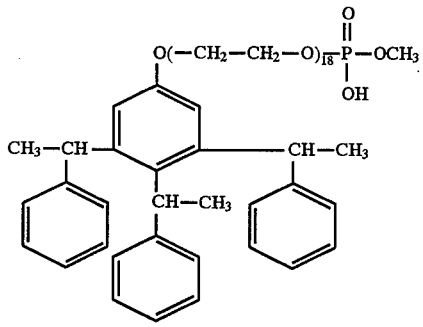

Demonstration of the Spreading and Permeation Capacity of the Inventive Concentrates and of Emulsions Prepared with Such Concentrates Method: TL-Plate 0,25 mm Silicagel 60F254 Merck Art. No. 11'798 with concentration zone.

Eluent: PBS Dulbecco's without Ca and Mg (=Ringer solution or physiological sodium chloride solution, buffered)

| Rf.-Values | |
|---|---|
| | Concentrate |
| 0,1% Substance, | in aquous |
| dissolved in | emulsion |
| dichlormethane | 1000 ppm. |
| Rf.-Values: | Rf.-Values: |
| Ergocalciferol-C 8:0 | 0 | 21,21 |
| Ergocalciferol-all trans retinate | 0 | 48,39 |
| Ergocalciferol-all trans retinate: | 0 | 45,45 |
| (with DL-α-tocopherol-acetate as coamulgator) | | |
| DL-α-tocopherol-C 8:0 | 0 | 21,21 |
| DL-α-tocopherol-10-undecenoate | 0 | 59,68 |
| DL-α-tocopherol-C 16:0 | 0 | 48,48 |

P.S.: Microemulsions 1:1000 = 1,000 ppm active subastance = 1 mg/ml.

The above indicated Rf.-Values illustrate the behaviour of the inventive concentrates in cell colonies and, more specifically, at the cell membrane. The reduced surface tension of the concentrates, with values of 30 to 32 mN/m, the small size of the generated micromicelles as well as the low viscosity of the microemulsion are all factors which influence the diffusion through the cell membrane and the spreading in the cell plasma in a very favourable manner. Control measurements, carried out at the Institute for Polymers, Swiss Federal Institute of Technology at Zurich, exhibited a radius for the micelles of around 1 nm. (Prof. Dr. Pier Luigi LUISI and Prof. Dr. Peter SCHURTENBERGER).

Example for the pharmaceutical production of a system's preparation containing the inventive concentrates in the form of "multiple units"

a) Granulation (Granules and Pellets)

| Metolose ® 90 SH-4000 (Shin-Etsu Chemical) | 90.0 g |
|---|---|
| Avicel ® PH-101 | 80,3 g |
| Inventive CONCENTRATE | 139,4 g |
| Aerosil ® 200 | 80,3 g |
| | 390.0 g |

Granulation in the high speed mixer or the fluidized bed, with the addition of 110 g ethanol, sieving on a 18 to 42 mesh screen with crushing, drying for 24 h at 40° C.

b) Enteric and Sustained Release Coating

In the fluidized bed with AQOAT® AS-HG (Shin-Etsu Chemical) and Talc c) Composition of Finished Granules or Micropellets

| Core Material | 44% by weight |
|---|---|
| Inventive CONCENTRATE | 25% by weight |
| Enteric coating | 31% by weight |
| | 100% |

N.B. The pellets or granules according to a) can also be filled without prior coating into capsules which are made of AQOATä (HPMC-AS-M or HPMC-AS-N), have been sealed with acetone/ethanol 1:1 and can thus perform the functions of pH-control and slow release.

BIOLOGICAL ASSAYS

The antitumour activity of spontaneously dispersible concentrates containing active substances prepared according to the examples No. 1 to 4 is confirmed by the following test results:

1. In-vitro Assays Using Suitable Tumour Cell Lines

A biological assay system using microtiter plates and serial dilutions has been developed. Batches of 104 tumour cells per ml were set up in culture medium RPMI 1640 and inactivated with 10% of fetal calf serum (GIBCO); they are spread at a density low enough to enable them to grow during the assay, in so-called non-confluent monolayers. Samples are added after 6–24 hours, with 100 μl per row, to which 100 μl of medium are added in the first well. Half of this mixture is withdrawn, transferred into the next well and again treated with 100 μl of medium, etc. This results in an n½ geometrical serial dilution.

In the plaque assay, the samples are incubated at 37° C. for 3 to 5 days under 3½% of $CO_2$. They are then stained and fixed using 0.1% crystal violet (Fluka, Buchs) in a solution of 70% of methanol, 1% of formaldehyde and 29% of water. The samples are evaluated under the microscope, magnification 300×. The greatest cytotoxic dilution is determined. The samples can also be evaluated quantitatively by means of scanning and absorption measurement in a spectrophotometer.

2. Evaluation of the Results a) TS/A-Assay: Greatest Celltoxic Dilution

| | TUMOUR LINE | |
|---|---|---|
| PREPARATION | TS/A:murine adenocarcinoma 24 h | In dilution active up to 1: 72h |
| $D_2$-C 4:1 | 20'480'000 | — |
| $D_2$-C 8:0 | 2'000'000 | 4'000'000 |
| $D_2$-C 11:1 | 40'960'000 | 163'840'000 |
| $D_2$-all trans-RET. | 16'000'000 | 64'000'000 |
| DL-α-TOCO-C 8:0 | 4'000'000 | 32'000'000 |

TSA: murine adenocarcinoma (spontaneous mammacarcinoma) Prof.Dott. Guido FORNI, Istituto di Microbiologia, Universita degli Studi di TORINO, Scuola di Medicina b) Py 6-ASSAY: Greatest Celltoxic Dilution

| | TUMOUR LINE | |
|---|---|---|
| PREPARATION | Py 6 (Polyoma transformed 3T3 mouse cells) 20 h | In dilution active up to 1: 60 h |
| D2-C 4:1 | 10'240'000 | — |
| D2-C 11:1 | 5'120'000 | — |
| D2-all trans-RET. | 16'000'000 | 32'000'000 |
| $D_2$-C 18:3 | 6'025'000 | 96'375'000 |
| $D_3$-C 18:3 | 6'000'000 | 24'000'000 |
| DL-α-TOCO-C 8:0 | 8'000'000 | 16'000'000 |
| DL-α-TOCO-C 11:1 | 12'000'000 | 48'000'000 |
| DL-α-TOCO-C 18:1 | 6'000'000 | 24'000'000 |
| DL-α-TOCO-C 18:3 | 6'025'000 | 48'200'000 |
| TOCO-a.t.-RETINAT | 12'000'000 | 96'000'000 |

Py 6: Polyoma-virus-transformed 3T3 mouse cells c) Other Tumor-cell-lines

| PREPARATION Exposure | TUMOUR LINES | | |
|---|---|---|---|
| | Y T 43 In dilution active up to 1: 4 days | P 815 In dilution active up to 1: 4 days | L 929 In dilution active up to 1: 2 days |
| CALCIOL-C 4:1 | 48'000'000 | 16'000'000 | 64'000'000 |
| CALCIOL-C 8:0 | 32'000'000 | 32'000'000 | 64'000'000 |
| CALCIOL-C 11:0 | 32'000'000 | 16'000'000 | 32'000'000 |
| CALC.-all trans-RET. | 128'000'000 | 64'000'000 | 128'000'000 |
| DL-α-TOCO-C 8:0 | 32'000'000 | 32'000'000 | 64'000'000 |
| DL-α-TOCO-C 16:0 | 16'000'000 | 16'000'000 | 64'000'000 |

Y T 43: ibridoma/anticorpi monoclonali (hybridoma cells)
P 815: mastocytoma
L 929: fibroblastoma (areolar and adipose tissue)
Prof. Guido Forni, Istituto di Microbiologia, Università degli Studi di Torino, Scuola di Medicina d) Cytotoxicity on Human Tumor Cell Lines

| | Survival rate in % (MTT-method with tetrazol blue) | | | |
|---|---|---|---|---|
| | CELL-LINE | | | |
| PREPARATION | ST-4 | RAJI | K 562 | H L 60 |
| DILUTION 1:1'000'000 | | | | |
| CALCIOL-CROTONATE | — | 8 | 3 | 9 |
| CALCIOL-CAPROYLATE | 1 | 7 | 8 | 7 |
| CALCIOL-C 11:1 | | | | |
| CALCIOL-all tr.-RET. | — | 9 | 3 | 8 |
| | 1 | 2 | 0 | 0 |
| TOCO-CAPROYLATE | 1 | 8 | 7 | 9 |
| TOCO-10-UNDECEN. | — | 1 | 1 | 0 |
| DILUTION 1:10'000'000 | | | | |
| CALCIOL-CROTONATE | 57 | 83 | 63 | 93 |
| CALCIOL-CAPROYLATE | 39 | 88 | 71 | 35 |
| CALCIOL-C 11:1 | | | | |
| CALCIOL-all tr.-RET. | 56 | 91 | 56 | 88 |
| | 64 | 36 | 85 | 13 |
| TOCO-CAPROYLATE | 41 | 73 | 85 | 56 |
| TOCO-10-UNDECEN. | 67 | 10 | 85 | 100 |

ST-4 Linfoma convoluto T
RAJI Leucemia linfoide B
K 562 Eritroleucemia
H L 60 Leucemia mieloide e) Testing a Concentrate-Mixture with $D_2$- and $D_3$-Ester Components

| | Intitumoral Activity on human cell-lines Killing rate in % | | |
|---|---|---|---|
| | CELL-LINES | | |
| CONCENTRATION | ST-4 | H L 60 | K 562 |
| 1:10'000'000 | 100 | 100 | 100 |
| 1:100'000'000 | 73 | 68 | 70 |
| 1:1'000'000'000 | 47 | 6 | 54 |

Human Tumour cell-lines:
ST-4 Linfoma convoluto T
HL 60 Leucemia mieloide
K 562 Eritoleucemia
CONCENTRATIONS:
relative to the total content of Calciol- and Cholecalciol esters
Tests conducted at the Ospedale maggiore San Giovanni Battista, LE MOLINETTE, Torino. Direction: Prof. Dott. Giorgio RIVARA.

Additional Tests with Human Tumor Cell-lines
BATTELLE INSTITUTE, Frankfurt, FRG. (Dr. Matthias GIESE) assessed the cytotoxic effect on various selected cell lines of solid human tumours, which grow relatively slowly. The assay was conducted with 2% concentrates (by weight) of:
A CALCIOL-CHOLECALCIOL-ESTER-MIXTURE 1*)
B DL-α-TOCOPHEROLESTER-MIXTURE 1*)
C CALCIOL-all trans-RETINATE
with the following tumor cell lines (provided by the German Cancer Research Center, DKFZ, Heidelberg, FRG):
1 EJ28: carcinoma of bladder
2 LX-1: carcinoma of lung N.B. 1*) Composition of A: equal parts by weight of the following five Calciol-esters: calciol-C 11:1, C 12:1, C 16:0, C 183 and all trans retinate; plus equal parts by weight of the following five Cholecalciol-esters: Cholecalciol-C 4:1, C 11:1, C 16:0, C 18:3 and all trans retinate. Composition of B: equal parts by weight of the following five DL-α-tocopherol-esters: Toco-C 8:0, C 11:1, C 16:0, C 183 and all trans retinate.

The following biological response modifiers (BRM) were used as controls:
a rhu Interferon-Gamma (Biozol, BRD)
b rhu Tumor-Necrosis Factor Alpha (Biozol, BRD)

Results are given in dilution series and using the $IC_{50}$-values as indicator. [Inhibitory concentration] Incubation of the cells for 24 h, and 72 h respectively, at 37° C.; vitality staining after 3 and 14 days. Testing range 1:106 to 1:109, calculated on the active substance content.

Smaller differences only between the individual cell lines became apparent, as well as relatively feeble differences between the the three concentrates. The $IC_{50}$-values are centered in the dilution range 1:107.

In summary, the findings of the tests demonstrate clearly and throughout a cytotoxic effect on the tumour cells and not merely a cytostatic effect.

The strongest cytotoxic effect was shown for the CALCIOL/CHOLECALCIOL-ESTER-MIXTURE. The control substances BRM, however, showed no measurable effect on either of the 2 cell lines included in the assay.

Diagram 1/13 FIG. 1 and 2: Cytotoxicity on human solid tumours. Vide the technical appendix.

In-vitro Assays Conducted by the National Cancer Institute, Bethesda

Broad systematic tests conducted by the NCI under their Developmental Therapeutics Program with 60 different cell-lines of human tumours covered 8 PANELS:
Leukemia
Non-small cell Lung Cancer
Small cell Lung Cancer
Colon Cancer
CNS Cancer
Melanoma
Ovarian Cancer
Renal Cancer The following measuring rods were applied:
PG (Percentage Growth)
Dose-Response-Curves
Mean Graphs The diagrams 2/13 to 13/13 with FIG. 3.1 to 27 render the overall results in graphical summaries for
CALCIOL-10-UNDECENOATE-CONCENTRATE
CALCIOL-all trans-RETINATE-CONCENTRATE and
CALCIOL-LINOLENATE-CONCENTRATE
Cf. the Technical Annexures.

The principal result of the extensive assessment by NCI is quite comparable to the findings reached by BATTELLE INSTITUTE, namely that the INVENTIVE CONCEN- TRATES not only show an anti-proliferation effect, i.e. a growth inhibition, but a true and general cytotoxicity. This is particularly marked with those cell lines which possess short doubling times and are thus relatively more sensitive to antitumour agents than the slower growing (solid) tumour lines.

Cf. also: Michael R. Boyd: Status of the NCI Preclincal Antitumor Drug Discovery Screen, PPO updates, Vol. 3, October 1989, Number 10. Anne Monks et al.: Feasibility of a High-flux Anticancer Drug Screen using a diverse Panel of cultured human Tumor Cell Lines, Journal of the National Cancer Institute, Vol. 83, No. 11, Jun. 5, 1991.

Proof of Membrane-penetration at the Single Tumour Cell

It can be shown with light microscopy—and also with Laser scanning microscopy, that few hours after incubation there is forming a halo of vacuoles around the nucleus of the cell [example Py6-cells of 3T3-mice); thinly disseminated, medium concentration (=dilution) of the active-substance containing concentrates].

The analytical demonstration that these vacuoles in fact contain the VITAMIN-STEROLESTER active substances is quite clear and unequivocal: it involves cleaning the incubated tumour cells, extracting the cell plasma with 1% SDS, centrifuguing, mixing the supernatant with a 0,05%-solution of Uvitex® CF conc. (CIBA-GEIGY) in acetone/water (85:15) or of Uvitex® EBF (CIBA-GEIGY) or of Tinopal® GS (CIBA-GEIGY).

The VITAMIN-STEROLESTERS according to the invention extinguish the fluorescence in the longwave UV-segment which is normally occasioned by the markers Uvitex® CF conc. and Uvitex® EBF, and Tinopal® GS respectively. The thin-layer plate shows blue coloring.

UV-scanning at 366 nm. Microdialysis (Micellar electro-kinetic capillary chromatography; MEEC) by means of capillary zone electrophoresis with a specialized buffer system and laser induced fluorescence detection (Beckman Instruments Pace 2000).

What we claim is:

1. A spontaneously dispersible concentrate which forms a microemulsion in water comprising:

0.001 to 15% by weight of an ester or a combination of esters of a vitamin-D compound according to one of formulae (I) to (IV):

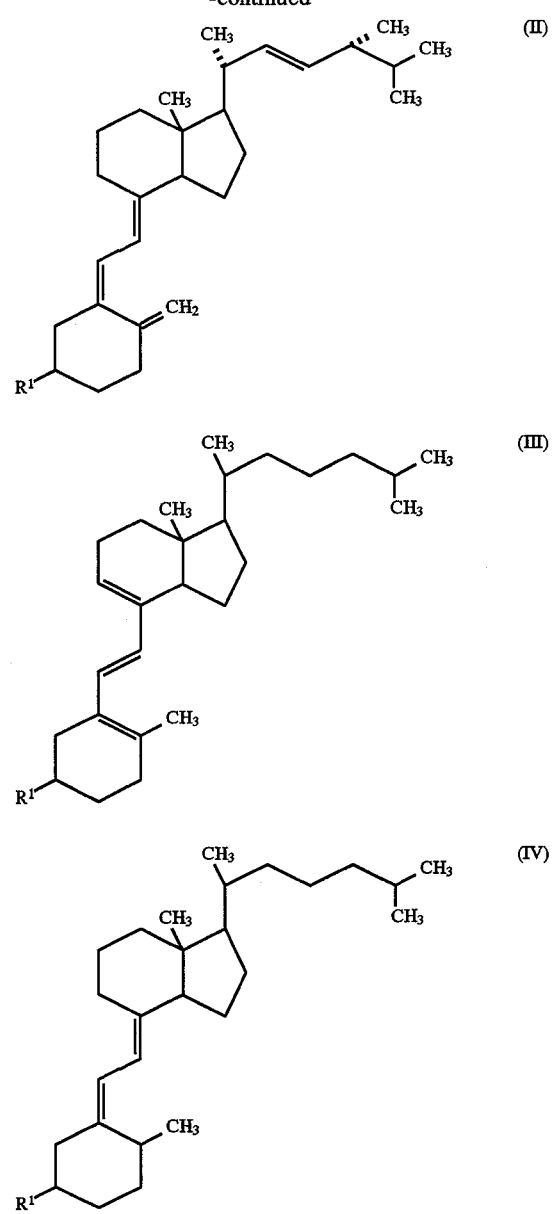

wherein $R^1$ is selected from the group consisting of a $C_{1-32}$ alkyl carbonyloxy, a $C_{2-32}$ alkenyl carbonyloxy, a $C_{2-32}$ alkapolyene carbonyloxy, a group of formula (V):

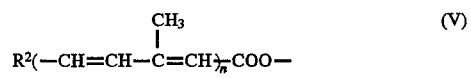

a group of formula (VI):

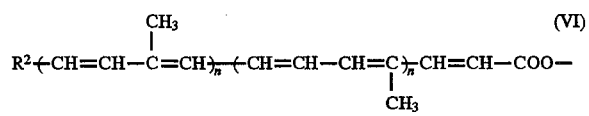

wherein n is 1, 2, 3, 4 or 5 and $R^2$ is a radical selected from the group consisting of 0 to 40% by weight of a solvent or solvent mixture which is pharmaceutically acceptable and is a hydrotropic or coemulsifier;

0.001 to 90% by weight of a pharmaceutically acceptable surfactant or surfactant mixture; and optionally up to 10% by weight of a vitamin or provitamin; and optionally up to 10% by weight of a free acid.

2. The spontaneously dispersible concentrate as claimed in claim 1 further comprising:

up to 45% by weight of a pharmaceutically acceptable non-ionic surfactant having a hydrophilic-lipophilic balance of between 2 and 18.

3. The spontaneously dispersible concentrate as claimed in claim 2 further comprising:

up to 45% by weight of a phosphoric acid ester tenside.

4. The spontaneously dispersible concentrate as claimed in claim 1 further comprising:

up to 45% by weight of a phosphoric acid ester tenside.

5. The spontaneously dispersible concentrate as claimed in claim 1 further comprising:

0 to 40% by weight of isopropylmyristate, isopropylpalmitate, or a neutral oil;

20 to 45% by weight of a 50:50 mixture of the two tensides:

and 20 to 45% by weight of a tert. octylphenylpolyoxyethylene ether having 9 to 10 oxyethylene groups;

wherein the ester or combination of esters of the vitamin-D compound is present in an amount of from 7.5 to 15% by weight.

6. The spontaneously dispersible concentrate as claimed in claim 1 further comprising:

0 to 40% by weight of isopropylmyristate, isopropylpalmitate, or a neutral oil;

20 to 45% by weight of the tenside:

and 20 to 45% by weight of a tert. octylphenylpolyoxyethylene ether having 9 to 10 oxyethylene groups;

wherein the ester or combination of esters of the vitamin-D compound is present in an amount of from 7.5 to 15% by weight.

7. A pharmaceutical composition comprising an antitumor effective amount of the spontaneously dispersible concentrate as claimed in claim 1 and up to 10% by weight of a pharmaceutically acceptable excipient, diluent, stabilizer, or combination thereof.

8. A pharmaceutical composition according to claim 7, wherein the spontaneously dispersible concentrate is present in an amount of from 1 to 95% by weight and the composition is in a unit-dosage form of capsules or ampules.

9. A pharmaceutical composition according to claim 7, wherein the spontaneously dispersible concentrate is present in an amount of from 1 to 95% by weight and the composition is in a dosage form selected from the group consisting of micropellets, granules, coated tablets, tablets, and suppositories.

10. A pharmaceutical composition according to claim 9, comprising 44 parts of a core material for granules or micropellets, 25 parts of the spontaneously dispersible concentrate, and 31 parts of an enteric, slow-release coating comprising hydroxypropyl-methylcellulose-acetate-succinate.

11. A pharmaceutical composition according to claim 7, comprising 64 parts of a core material for granules or micropellets and 36 parts of the spontaneously dispersible concentrate, which is filled into capsules made from hydroxypropyl-methylcellulose-acetate-succinate.

* * * * *